(12) United States Patent
McCaslin et al.

(10) Patent No.: US 10,624,306 B1
(45) Date of Patent: Apr. 21, 2020

(54) ALFALFA VARIETY 412A122

(71) Applicant: Forage Genetics International, LLC, West Salem, WI (US)

(72) Inventors: Mark McCaslin, Shoreview, MN (US); Peter Reisen, Nampa, ID (US)

(73) Assignee: Forage Genetics International, LLC, West Salem, WI (US)

( * ) Notice: Subject to any disclaimer, the term of this patent is extended or adjusted under 35 U.S.C. 154(b) by 0 days.

(21) Appl. No.: 16/254,927

(22) Filed: Jan. 23, 2019

(51) Int. Cl.
*A01H 6/54* (2018.01)
*A01H 5/10* (2018.01)

(52) U.S. Cl.
CPC ............ *A01H 6/544* (2018.05); *A01H 5/10* (2013.01)

(58) Field of Classification Search
None
See application file for complete search history.

(56) References Cited

U.S. PATENT DOCUMENTS

| | | | |
|---|---|---|---|
| 7,288,697 B2 * | 10/2007 | Johnson | A01H 5/10 800/298 |
| 7,566,817 B2 | 7/2009 | Beazley et al. | |
| 8,124,848 B2 | 2/2012 | Beazley et al. | |
| 9,068,196 B2 | 6/2015 | Beazley et al. | |
| 9,670,498 B2 | 6/2017 | Levering et al. | |
| 9,701,976 B2 | 7/2017 | Levering et al. | |
| 9,854,778 B2 | 1/2018 | Hiatt | |

OTHER PUBLICATIONS

Moore (Association of Official Seed Certifying Agencies, "2018 Alfalfa and Miscellaneous Legumes Variety Review Board Report," pp. 1-96, published Jan. 24, 2018).*
U.S. Appl. No. 16/254,843, filed Jan. 23, 2019, Reisen et al.
U.S. Appl. No. 16/254,959, filed Jan. 23, 2019, Reisen et al.
U.S. Appl. No. 16/254,866, filed Jan. 23, 2019, Reisen et al.
U.S. Appl. No. 16/254,971, filed Jan. 23, 2019, McCaslin et al.
U.S. Appl. No. 16/254,999, filed Jan. 23, 2019, Reisen et al.
U.S. Appl. No. 16/254,943, filed Jan. 23, 2019, McCaslin et al.
U.S. Appl. No. 16/255,023, filed Jan. 23, 2019, McCaslin et al.
U.S. Appl. No. 16/255,307, filed Jan. 23, 2019, McCaslin et al.
U.S. Appl. No. 16/255,257, filed Jan. 23, 2019, Reisen et al.
U.S. Appl. No. 16/255,282, filed Jan. 23, 2019, Reisen et al.
U.S. Appl. No. 16/255,330, filed Jan. 23, 2019, Ho et al.
U.S. Appl. No. 16/255,351, filed Jan. 23, 2019, Ho et al.
U.S. Appl. No. 16/255,372, filed Jan. 23, 2019, Ho et al.
U.S. Appl. No. 16/255,393, filed Jan. 23, 2019, Ho et al.
U.S. Appl. No. 16/255,050, filed Jan. 23, 2019, Rodgers et al.
U.S. Appl. No. 16/255,411, filed Jan. 23, 2019, Rodgers et al.
U.S. Appl. No. 16/255,431, filed Jan. 23, 2019, McCaslin et al.
U.S. Appl. No. 16/255,463, filed Jan. 23, 2019, McCaslin et al.
U.S. Appl. No. 16/255,478, filed Jan. 23, 2019, McCaslin et al.
U.S. Appl. No. 16/255,490, filed Jan. 23, 2019, McCaslin et al.
U.S. Appl. No. 16/255,509, filed Jan. 23, 2019, Reisen et al.
U.S. Appl. No. 16/255,534, filed Jan. 23, 2019, Reisen et al.
U.S. Appl. No. 16/255,555, filed Jan. 23, 2019, Reisen et al.
U.S. Appl. No. 16/255,574, filed Jan. 23, 2019, McCaslin et al.
U.S. Appl. No. 16/255,590, filed Jan. 23, 2019, Rodgers et al.
U.S. Appl. No. 16/255,602, filed Jan. 23, 2019, Rodgers et al.
U.S. Appl. No. 16/255,615, filed Jan. 23, 2019, Rodgers et al.
U.S. Appl. No. 16/255,626, filed Jan. 23, 2019, Rodgers et al.
Association of Official Seed Certifying Agencies, "2018 Alfalfa and Miscellaneous Legumes Variety Review Board Report," pp. 1-101, available at: https://www.aosca.org/wp-content/uploads/2018/08/2018AL_Report_FINAL-1.pdf, published Jan. 24, 2018.
Larkin et al., "Somaclonal variation—a novel source of variability from cell cultures for plant improvement," *Theor Appl Genet*, 60(4):197-214; 1981.
Moose et al., "Molecular plant breeding as the foundation for 21st century crop improvement," *Plant Physiol*, 147(3):969-77, 2008.
Variety specific information as indicated in transmittal letter of Information Disclosure Statement for U.S. Appl. No. 16/254,927, filed Jul. 8, 2019.

* cited by examiner

*Primary Examiner* — Vinod Kumar
(74) *Attorney, Agent, or Firm* — Dentons US LLP

(57) ABSTRACT

The invention relates to the alfalfa variety designated 412A122. Provided by the invention are the seeds, plants and derivatives of the alfalfa variety 412A122. Also provided by the invention are tissue cultures of the alfalfa variety 412A122 and the plants regenerated therefrom. Still further provided by the invention are methods for producing alfalfa plants by crossing the alfalfa variety 412A122 with itself or another alfalfa variety and plants produced by such methods.

27 Claims, No Drawings

ALFALFA VARIETY 412A122

BACKGROUND OF THE INVENTION

Field of the Invention

The present invention relates generally to the field of alfalfa breeding. In particular, the invention relates to the novel alfalfa variety 412A122.

Description of Related Art

There are numerous steps in the development of any novel plant germplasm. Plant breeding begins with the analysis and definition of problems and weaknesses of the current germplasm, the establishment of program goals, and the definition of specific breeding objectives. The next step is selection of germplasm that exhibit the traits to meet the program goals. The goal is to combine in a single variety an improved combination of traits from the parental germplasm. These selection traits may include higher forage yield; increased seed yield; improved feed quality, including improved digestability and improved milk conversion by ruminant animals; resistance to diseases and insects; augmented stems and roots; increased abiotic stress tolerance; increased drought and heat tolerance; strong stand establishment; improved agronomic quality and standability traits; resistance to herbicides; winter hardiness; and improvements in compositional traits to meet current and future agronomic practices.

Alfalfa (*Medicago sativa* L.), also known as lucerne, is a valuable forage legume. Thus, a goal of plant breeders is to develop stable, high-yielding alfalfa varieties that are agronomically sound. The reasons for this goal include, but are not limited to, maximizing the amount of commodity plant product, e.g., hay, pasture, and silage, produced on the land used; supplying food for humans and animals; and replenishing nutrients depleted from the soil. To accomplish this goal, the breeder must select and develop alfalfa plants that have the traits that result in agronomically superior varieties.

Alfalfa is grown worldwide as forage for livestock, especially cattle. Alfalfa is among the highest-yielding forage crop species, but it is the combination of high yield and nutritional quality that make alfalfa such a valuable crop. Alfalfa is most often harvested as hay, but is also grazed, made into silage, and fed as greenchop. Alfalfa is primarily used to feed high-producing dairy cows, but is also a food source for beef cattle, horses, sheep, goats, rabbits, and poultry. Humans consume alfalfa sprouts and incorporate dehydrated alfalfa into dietary supplements.

Alfalfa, like other legumes, have root nodules that contain *Sinorhizobium meliloti*, bacteria that are effective at fixing nitrogen. Alfalfa therefore is also utilized to replenish nitrogen following crops without the ability to fix nitrogen in crop rotation.

The commercial production of seeds for growing alfalfa varieties normally involves three stages, the production of breeder, foundation, and then certified seed. Breeder seed is the initial seed produced by an intercross of selected parental plants, and thus represents the initial generation of an experimental cultivar. A portion of the breeder seed is then used for small plot forage trials and characterization of the alfalfa variety. Another portion of the breeder seed can be grown in isolation from other alfalfa plants to produce the foundation seed. Foundation seed is then grown in isolation from other alfalfa plants to produce the certified seed. The certified seed is typically what is sold for commercial crop production. Allele frequencies across breeder, foundation, and certified seed are maintained.

SUMMARY OF THE INVENTION

One aspect of the present invention relates to seed of alfalfa variety 412A122. Another aspect of invention relates to plants produced by growing a seed of alfalfa variety 412A122 and any plant part thereof. A plant part as recited herein may be, but is not limited to, leaves, roots, root tips, root hairs, anthers, pistils, stamens, pollen, ovules, flowers, seeds, embryos, stems, buds, cotyledons, hypocotyls, cells and protoplasts. The invention further provides a tissue culture of regenerable cells or protoplasts and the alfalfa plants that may be regenerated from such a tissue culture. The regenerable cells and protoplasts of the invention may be derived from a plant of alfalfa variety 412A122 or plant part thereof, and the plants regenerated therefrom are capable of expressing all the morphological and physiological characteristics of a plant grown from a seed of alfalfa variety 412A122.

In a further aspect, the invention provides a composition comprising a seed of alfalfa variety 412A122 that is comprised in plant seed growth media. In certain embodiments, the plant seed growth media is a soil or synthetic cultivation medium. In specific embodiments, the growth media may be comprised in a container or may, for example, be soil in a field. Plant seed growth media are well known to those of skill in the art and include, but are in no way limited to, soil or synthetic cultivation medium. Plant seed growth media can provide adequate physical support for seeds and can retain moisture and/or nutritional components. Examples of characteristics for soils that may be desirable in certain embodiments can be found, for instance, in U.S. Pat. Nos. 3,932,166 and 4,707,176. Synthetic plant cultivation media are also well known in the art and may, in certain embodiments, comprise polymers or hydrogels, and examples of such compositions are described, for example, in U.S. Pat. No. 4,241,537.

A further aspect of the invention is a method for producing a first generation of progeny alfalfa seed. The method comprises crossing a plant of alfalfa variety 412A122 with itself or a second alfalfa plant and harvesting the resultant alfalfa seed. In particular embodiments, the second alfalfa plant may be another plant of alfalfa variety 412A122. The invention further provides for the first generation alfalfa seed produced by this method and the plants grown from those seeds.

Another embodiment of the invention is a method of vegetatively propagating a plant of alfalfa variety 412A122. The method comprising the steps of: (a) collecting a tissue capable of being propagated from a plant of alfalfa variety 412A122; (b) cultivating that tissue to obtain proliferated shoots; and (c) rooting those proliferated shoots to obtain rooted plantlets. In particular embodiments, this method further comprises the following step: (d) growing a plant from the rooted plantlets.

The invention further provides for a method of modifying a plant of alfalfa variety 412A122. The method comprises introducing a transgene or a single locus conversion into a plant of alfalfa variety 412A122. The invention also provides for the alfalfa plants produced by this method. In specific embodiments, the plants produced by this method comprise a transgene or single locus that comprises a nucleic acid sequence that enables site-specific genetic recombination or confers a trait selected from the group consisting of male sterility, herbicide tolerance, insect resistance, pest resistance, disease resistance, improved digestibility, improved energy content, improved forage or seed yield, improved winterhardiness, improved nitrogen fixation, modified fatty acid metabolism, abiotic stress resistance, flowering time, altered seed amino acid composition, and modified carbohydrate metabolism. The seeds that produce the plants generated by this method are also contemplated by the invention.

Still yet another embodiment of the invention is a method to introduce a single-locus conversion into a plant of alfalfa variety 412A122. The method comprises the following steps: (a) crossing a plant of alfalfa variety 412A122 with a second alfalfa plant to produce a first generation of progeny plants, wherein the second alfalfa plant comprises the single locus; and (b) selecting a progeny plant that comprises the single locus. In specific embodiments, the single locus introduced into a plant of alfalfa variety 412A122 comprises a transgene. Still yet another embodiment of this invention is a method for introducing a transgene or a single locus conversion into a population of alfalfa plants. This method comprises the following steps: (a) modifying a plant of alfalfa variety 412A122 by introducing a transgene or a single locus conversion; and (b) crossing that modified alfalfa plant with a population of alfalfa plants to produce a population of progeny plants, wherein at least a progeny plant comprises the transgene or single locus conversion. In particular embodiments, this method further comprises the following step: (c) applying selection techniques to the population produced in step (b) to select the progeny plants that comprise the transgene or single locus conversion. The invention further provides for the alfalfa plants produced by this and the foregoing method as well as the seeds that can produce these plants.

Another embodiment provided by this invention is a method of producing a synthetic alfalfa variety. The method comprises combining the seed of alfalfa variety 412A122 with the seed of a second alfalfa variety. Yet another embodiment is a method of producing a commodity plant product. This method comprises producing the commodity plant product from a plant of alfalfa variety 412A122. In specific embodiments the commodity plant product is selected from a group consisting of sprouts, forage, hay, greenchop, and silage. The invention further provides for the commodity plant product produced by this method, wherein the commodity plant product comprises at least one cell of alfalfa variety 412A122.

DETAILED DESCRIPTION OF THE INVENTION

The instant invention provides methods and composition relating to plants, seeds, and derivatives of alfalfa variety 412A122. Alfalfa variety 412A122 is adapted to the North Central, East Central, Winterhardy Intermountain, and Moderately Winterhardy Intermountain regions and is very winterhardy. Alfalfa variety 412A122 has been tested in Washington, Idaho, Iowa, Wisconsin and Pennsylvania. Alfalfa variety 412A122 is suitable for use in producing hay, haylage, greenchop or dehydration.

Alfalfa variety 412A122 is a synthetic variety with 110 parent plants. Parent clones were selected for forage yield, persistence and resistance to one or more of the following pests: bacterial wilt, *Fusarium* wilt, *Verticillium* wilt, anthracnose, *Phytophthora* root rot, stem nematode, northern root knot nematode and *Aphanomyces* root rot (Race 1 and Race 2). Phenotypic selection was used to identify the parent plants. The following germplasm sources were used in the development of this variety: various FGI experimental populations (100%). Syn1 seed was harvested in total on all parents and bulked to form breeder seed in 2012.

Alfalfa variety 412A122 is a Moderately Dormant variety similar to check variety FD4. Alfalfa variety 412A122 flower color is 94% purple, 2% variegated, 2% cream, 1% yellow with a trace of white.

The total yield, mean annual yield, persistence, fall dormancy, and winter survival of alfalfa variety 412A122 were also analyzed and comparisons were made with selected varieties. The results of these analyses are presented in the tables that follow.

Alfalfa variety 412A122 is resistant to highly resistant to anthracnose (Race 1), bacterial wilt, *Fusarium* wilt, *Verticillium* wilt, *Phytophthora* root rot, *Aphanomyces* root rot (Race 1), *Aphanomyces* root rot (Race 2), and stem nematode. All disease and pest tests of alfalfa variety 412A122 were conducted for the National Alfalfa and Miscellaneous Legume Variety Review Board AOSCA certification and were conducted by standard procedures and scoring systems as described in the NAAIC Standard Tests to Characterize Alfalfa Cultivars, which are maintained online on the NAAIC's website. The results of these analyses are presented in the tables that follow.

TABLE 1

Total yield of alfalfa variety 412A122 compared to other varieties at multiple locations.

| Test Location | Mo/Yr Planted | Year Harvested | No. Cuts | 412A122 (Syn 1) | Check 1: WL 354HQ | Check 2: 54V09 | Check 3: HybriForce 2400 | LSD .05 | CV % |
|---|---|---|---|---|---|---|---|---|---|
| West Salem, WI | August 2012 | 2013 | 4 | 7.80 | 7.79 | 7.37 | 7.44 | 0.38 | 3.58 |
| | | 2014 | 4 | 6.94 | 5.62 | 5.39 | 5.25 | 0.38 | 4.21 |
| | | 2015 | 4 | 7.96 | 6.58 | 5.19 | 5.2 | 0.49 | 5.02 |
| Boone, IA | August 2012 | 2013 | 3 | 4.73 | 5.15 | 4.98 | 5.09 | 0.85 | 12.93 |
| | | 2014 | 4 | 5.86 | 5.55 | 5.44 | 5.59 | 0.79 | 10.47 |
| Nampa, ID | August 2012 | 2013 | 6 | 11.13 | 10.5 | 9.61 | 10.42 | 1.16 | 7.36 |
| | | 2014 | 6 | 9.58 | 9.54 | 7.82 | 8.88 | 2.00 | 14.97 |
| | | 2015 | 1 | 2.83 | 2.82 | 2.85 | 3.13 | 0.55 | 13.59 |
| Mount Joy, PA | August 2012 | 2013 | 5 | 8.09 | 7.70 | 8.08 | 7.68 | 0.73 | 6.80 |
| | | 2014 | 5 | 9.74 | 9.11 | 9.02 | 8.86 | 0.82 | 6.50 |
| Touchet, WA | May 2013 | 2014 | 5 | 14.02 | 13.56 | 12.58 | 12.35 | 1.08 | 4.95 |
| | | 2015 | 5 | 13.16 | 12.8 | 11.81 | 11.67 | 1.20 | 5.66 |

TABLE 2

Mean annual yield of alfalfa variety 412A122.

| Variety names | # of Years Harvested | Total # of Harvests | 412A122 (Syn 1) | Check 1: WL 354HQ | Check 2: 54V09 | Check 3: HybriForce 2400 |
|---|---|---|---|---|---|---|
| 412A122 (Syn 1) | 12 | 52 | 8.49 | | | |
| Check 1: WL 354HQ | 12 | 52 | 8.49 | 8.06 | | |
| Check 2: 54V09 | 12 | 52 | 8.49 | | 7.51 | |
| Check 3: HybriForce 2400 | 12 | 52 | 8.49 | | | 7.63 |

TABLE 3

Persistence of alfalfa variety 412A122 compared to other varieties.

| Test Location | Mo/Yr Seeded | No. of Years Harvested | No. of Harvests | Mo/Yr of Readings Initial/Final | 412A122 (Syn 1) Initial/Final | HybriForce 2400 Initial/Final | 54V09 Initial/Final | LSD .05 | CV % |
|---|---|---|---|---|---|---|---|---|---|
| W Salem, WI | August 2012 | 3 | 12 | (September 2012)/(September 2015) | 100/82 | 100/69 | 100/75 | 6.9 | 9.2 |

TABLE 4

Fall dormancy of alfalfa variety 412A122 as determined from spaced plantings relative to three check varieties.

| Variety | Fall Dormancy Class | Unadjusted FDR | |
|---|---|---|---|
| 412A122 (Syn 1) | 4 | 4.1 | |
| 5246 | 3 | 3.1 | D |
| Legend | 4 | 4.0 | MD |
| Archer | 5 | 4.9 | MD |
| Test Mean: | | 4.3 | |
| L.S.D.(0.05%) | | 0.14 | |
| C.V. (%) | | 3.33 | |

Test conducted in 2012 by Forage Genetics at West Salem WI. Date of Last Cut (Mo/Yr): September 2012. Date Measured (Mo/Yr): October 2012. VD (Very Dormant)/D (Dormant)/MD(Moderately Dormant)/ND (Non-Dormant)/VND (Very Non-Dormant).

TABLE 5

Winter survival rating of alfalfa variety 412A122 compared to other varieties.

| Test Location | Mo/Yr Planted | Mo/Yr Measured | 412A122 (Syn 1) | ZG 9830 -1- | 5262 -2- | WL325 HQ -3- | G-2852 -4- | Archer -5- | CUF 101 -6- | LSD .05 | CV % |
|---|---|---|---|---|---|---|---|---|---|---|---|
| W. Salem, WI | May 2012 | May 2013 | 1.9 | 1.2 | 1.9 | 2.7 | 3.6 | 4.5 | 5.1 | 0.45 | 16.4 |
| Boone, IA | May 2012 | May 2013 | 1.7 | 1.3 | 1.7 | 2.6 | 3.7 | 4.3 | 5.0 | 0.22 | 7.2 |

1 = Extremely Winterhardy; 2 = Very Winterhardy; 3 = Winterhardy; 4 = Moderately Winterhardy; 5 = Slightly Winterhardy; and 6 = Non-Winterhardy.

TABLE 6

MULTIFOLIOLATE LEAF EXPRESSION score for alfalfa variety 412A122.

| Variety 412A122 (Syn 1) | | Multifoliolate Leaf Expression Score | MFI | % MF |
|---|---|---|---|---|
| | Range | High | 3.05 | 85 |
| Legend | 1.40-2.40 | Low | 1.47 | 54 |
| MultiKing I | 2.00-3.00 | Moderate | 2.11 | 73 |
| Proof | 2.80-3.80 | High | 3.34 | 90 |
| | | Test Mean: | 2.31 | 69 |
| | | L.S.D. (.05%) | 0.66 | 14.0 |
| | | C.V. (%) | 21.4 | 15.1 |

Test conducted in 2015 by Forage Genetics at Nampa, ID

TABLE 7

ANTHRACNOSE DISEASE (Race 1) score for alfalfa variety 412A122.

| Variety 412A122 (Syn 1) | Resistance Class HR | Unadjusted % R 39 | Adjusted % R 55 |
|---|---|---|---|
| Arc | HR | 46 | 65 |
| Saranac | S | 1 | 1 |
| Test Mean: | | 39 | 55 |
| L.S.D. (.05%) | | 9 | |
| C.V. (%) | | 16.8 | |

Test conducted in 2012 by Forage Genetics at West Salem, WI. Kind of test conducted: Greenhouse. S = <6%, LR = 6-14%, MR = 15-30%, R = 31-50%, HR = >50%.

TABLE 8

BACTERIAL WILT DISEASE score for alfalfa variety 412A122.

| Variety 412A122 (Syn 1) | Resistance Class HR | Unadjusted % R 62 | Adjusted % R 71 |
|---|---|---|---|
| Vernal | R | 37 | 42 |
| Sonora | S | 0 | 0 |
| Test Mean: | | 58 | 66 |
| L.S.D. (.05%) | | 13 | |
| C.V. (%) | | 16.5 | |

Test conducted in 2015 by Forage Genetics at West Salem, WI. Kind of test conducted: Field. S = <6%, LR = 6-14%, MR = 15-30%, R = 31-50%, HR = >50%.

TABLE 9

FUSARIUM WILT DISEASE score for alfalfa variety 412A122.

| Variety | Resistance Class | Unadjusted % R | Adjusted % R |
|---|---|---|---|
| 412A122 (Syn 1) | HR | 78 | 73 |
| Agate GH | R | 48 | 45 |
| MNGN-1 | S | 3 | 3 |
| | Test Mean: | 53 | 50 |
| | L.S.D. (.05%) | 16 | |
| | C.V. (%) | 19.0 | |

Test conducted in 2014 by Forage Genetics at Nampa, ID. Kind of test conducted: Greenhouse. S = <6%, LR = 6-14%, MR = 15-30%, R = 31-50%, HR = >50%.

TABLE 10

VERTICILLIUM WILT DISEASE score for alfalfa variety 412A122.

| Variety | Resistance Class | Unadjusted % R | Adjusted % R |
|---|---|---|---|
| 412A122 (Syn 1) | HR | 65 | 67 |
| Oneida VR | HR | 58 | 60 |
| Saranac | S | 3 | 3 |
| | Test Mean: | 31 | 32 |
| | L.S.D. (.05%) | 7 | |
| | C.V. (%) | 16.8 | |

Test conducted in 2013 by Forage Genetics at Nampa, ID. Kind of test conducted: Greenhouse. S = <6%, LR = 6-14%, MR = 15-30%, R = 31-50%, HR = >50%.

TABLE 11

PHYTOPHTHORA ROOT ROT DISEASE score for alfalfa variety 412A122.

| Variety | Resistance Class | Unadjusted % R | Adjusted % R |
|---|---|---|---|
| 412A122 (Syn 1) | HR | 51 | 56 |
| WAPH-1 | HR | 50 | 55 |
| Saranac | S | 0 | 0 |
| | Mean: | 51 | 56 |
| | L.S.D. (.05%) | 7 | |
| | C.V. (%) | 8.0 | |

Test conducted in 2011 by Forage Genetics at West Salem, WI. Kind of test conducted: Seedling. S = <6%, LR = 6-14%, MR = 15-30%, R = 31-50%, HR = >50%.

TABLE 12

APHANOMYCES ROOT ROT (RACE 1) DISEASE score for alfalfa variety 412A122.

| Variety | Resistance Class | Unadjusted % R | Adjusted % R |
|---|---|---|---|
| 412A122 (Syn 1) | HR | 62 | 66 |
| WAPH-1 (Race 1) | R | 47 | 50 |
| Saranac (Races 1 & 2) | S | 0 | 0 |
| | Test Mean: | 51 | 54 |
| | L.S.D. (.05%) | 7 | |
| | C.V. (%) | 8.0 | |

Test conducted in 2011 by Forage Genetics at West Salem, WI. Kind of test conducted: Greenhouse. S = <6%, LR = 6-14%, MR = 15-30%, R = 31-50%, HR = >50%.

TABLE 13

STEM NEMATODE score for alfalfa variety 412A122.

| Variety | Resistance Class | Unadjusted % R | Adjusted % R |
|---|---|---|---|
| 412A122 (Syn 1) | HR | 63 | 57 |
| Lahontan | R | 44 | 40 |
| Ranger | LR | 12 | 11 |

TABLE 13-continued

STEM NEMATODE score for alfalfa variety 412A122.

| Variety | Resistance Class | Unadjusted % R | Adjusted % R |
|---|---|---|---|
| 412A122 (Syn 1) | HR | 63 | 57 |
| | Test Mean: | 31 | 28 |
| | L.S.D. (.05%) | 9 | |
| | C.V. (%) | 16.6 | |

Test conducted in 2016 by Forage Genetics at Nampa, ID. Kind of test conducted: Greenhouse. S = <6%, LR = 6-14%, MR = 15-30%, R = 31-50%, HR = >50%.

TABLE 14

APHANOMYCES ROOT ROT (RACE 2) DISEASE score for alfalfa variety 412A122.

| Variety | Resistance Class | Unadjusted % R | Adjusted % R |
|---|---|---|---|
| 412A122 (Syn 1) | HR | 54 | 61 |
| WAPH-5 | R | 44 | 50 |
| Saranac | S | 1 | 1 |
| WAPH-1 | S | 1 | 1 |
| | Test Mean: | 43 | 49 |
| | L.S.D. (.05%) | 6 | |
| | C.V. (%) | 7.9 | |

Test conducted in 2012 by Forage Genetics at West Salem, WI. Kind of test conducted: Lab. S = <6%, LR = 6-14%, MR = 15-30%, R = 31-50%, HR = >50%.

Breeding Alfalfa Variety 412A122

One aspect of the current invention concerns methods for crossing alfalfa variety 412A122 with itself or a second plant and the seeds and plants produced by such methods. These methods can be used to further propagate alfalfa variety 412A122 by increasing the volume of seed available to farmers for the commercial production of commodity products. Or, these methods can be used to produce novel alfalfa strains and varieties. Alfalfa variety 412A122 is well-suited to the development of new strains and varieties based on the elite nature of its genetic background.

The goal of plant breeding is to develop new, unique, and agronomically superior varieties. The breeding and selection methods employed to do this depend on the mode of plant reproduction, the heritability of the trait(s) being improved, and the type of variety used commercially, e.g., synthetic variety, $F_1$ hybrid variety, pureline variety, etc. Alfalfa breeding is particularly complex because alfalfa has an autotetraploid genome and is normally self-incompatible, i.e., little or no viable seed is produced when alfalfa is selfed. Producing true breeding alfalfa parents is therefore not possible by traditional inbreeding techniques, and alfalfa breeders must be careful to avoid inbreeding depression when cross-breeding very small alfalfa populations. Inbreeding depression in alfalfa populations can result in reduced yield performance, loss of traits of interest as well as a decline in agronomic performance.

To improve alfalfa germplasm pools or varieties, a breeder will initially polycross two or more plants, generally using insect pollinators, and grow the resulting seed. These progeny plants are evaluated over multiple years and geographical, climatic, and soil conditions. Based on these field evaluations, a breeder will select the plants from this progeny population to advance to another generation of intermating and selection. These progeny plants are typically intermated, and the resultant seed is grown, often in half-sib rows, and evaluated in field trials. This process of evaluating, selecting, advancing, and intermating may continue iteratively for multiple cycles. Throughout this entire process, a breeder is simultaneously selecting the individual plants that will be incorporated into a distinct "parental" population which will be intermated to generate the new alfalfa variety. These "parental" plants can be selected at any stage in the breeding process and a breeder will typically select two to hundreds of "parental" plants to generate a new alfalfa variety.

The individual morphological and physiological characteristics of the alfalfa varieties that are developed by the above process as well as their cumulative morphological and physiological profiles, which are each unique composites of these individual characteristics, cannot be entirely or precisely expected or predicted at the outset of such a process. This is because all plant selections occur in unique environments with no control over the chromosomal segregation that is occurring at the DNA level (using conventional breeding procedures), and therefore millions of different genetic combinations, if not more, are possible. At the outset of any alfalfa breeding program, a breeder of ordinary skill in the art cannot expect or predict the final resulting varieties, except potentially in a gross and general fashion, and the same breeder would not expect to produce the same variety twice by merely intermating the exact same original "parental" plants and employing the same selection techniques. This unpredictability results in the expenditure of large amounts of research monies to develop agronomically superior new alfalfa varieties.

An advanced experimental population is evaluated with check varieties in environments that are representative of the commercial target area(s). The best lines are selected as new commercial varieties. These varieties may be used as parents to produce future populations for further selection. These processes, which lead to the final step of marketing and distribution, may take as much as 8 to 12 years from the time the first cross is made. Development of new alfalfa varieties is a time-consuming process that requires precise breeding skill, forward planning, and focused directional changes.

In selecting plants to cross with a plant of alfalfa variety 412A122 for the purpose of developing unique future novel alfalfa varieties, one of skill in the art would typically select those plants that exhibit one or more agronomically significant characteristics that are distinct from those exhibited by alfalfa variety 412A122, such as, but not limited to, disease, insect, or nematode resistance, herbicide tolerance, persistence, adaptation to specific environments, increased forage yield, and improved forage quality.

The true genotypic value for most traits can be masked by other confounding traits or environmental factors. The complexity of inheritance of any trait may influence the choice of selection method. The evaluation and identification of a superior individual alfalfa plant is based on the observed performance of that variety relative to that of standard commercial check varieties and other experimental varieties. Replicated observations, e.g., progeny test, provide a better prediction of genetic worth than single observations for traits with low heritabiltiy. In contrast, evaluating individual plants at a single location may be sufficient for selecting highly heritable traits.

The development of agronomically superior alfalfa plants may also be facilitated by employing specific breeding strategies. Popular selection methods that incorporate breeding strategies commonly include pedigree selection, modified pedigree selection, mass selection, recurrent selection, and backcrossing. Again, the means by which alfalfa reproduces, the expected degree of inbreeding depression, and the heritability of a particular trait may influence the choice of breeding method. Backcross breeding is used to transfer one or more genes for a highly heritable trait into an agronomically superior variety. For instance, this approach has been used extensively for breeding disease-resistant varieties (Bowers et al., Crop Sci., 32(1):67-72, 1992; Nickell and Bernard, Crop Sci., 32(3):835, 1992). Whereas, various recurrent selection techniques can be used to augment quantitatively inherited traits that can be controlled by numerous genes.

Recurrent selection is another method used to develop varieties from breeding populations. Breeding populations combine traits from two or more varieties or various broad-based sources into breeding pools from which varieties are developed by intermating and the subsequent selection of individuals based on phenotype. Mass or recurrent selection can be applied to improve populations of cross-pollinating crops like alfalfa. A genetically heterogeneous population, primarily consisting of heterozygous individuals, is either identified or created by intercrossing several different parents selected for individual agronomically significant characteristics, outstanding progeny, or excellent combining ability. The selected plants are then intermated to produce a new population upon which further cycles of selection are applied.

Backcross breeding has been used to transfer genetic loci for simply inherited or highly heritable traits into a variety that is used as the recurrent parent. The initial source of the trait to be transferred is called the donor or non-recurrent parent. After the $F_1$ cross, individuals possessing the phenotype or genotype of the donor parent are selected and then may be repeatedly crossed, i.e., backcrossed, to the recurrent parent or a close relative of the recurrent parent, i.e., modified backcross. The resulting plants are expected to resemble the recurrent parent and are converted for the genetic locus selected from the donor parent.

In half-sibling selection, a plant is randomly pollinated by a population of plants, and the half-sib seed produced by that female parent plant then are grown in progeny rows. The characteristics of those progeny rows are then evaluated to inform female parent selection.

Descriptions of other breeding methods that are commonly used for different traits and crops can be found in one of several reference books (e.g., Allard, "Principles of Plant Breeding," John Wiley & Sons, NY, University of California, Davis, Calif., 50-98, 1960; Simmonds, "Principles of Crop Improvement," Longman, Inc., NY, 369-399, 1979; Sneep et al., "Plant breeding perspectives," Wageningen (ed), Centre for Agricultural Publishing and Documentation, 1979; and Poehlman and Sleper, "Breeding Field Crops", 4th Ed., Iowa State University Press, Ames, 1995).

Testing of a novel alfalfa variety should detect any major faults and establish the level of superiority or improvement over current varieties as well as characterize the improved phenotypic performance of the new variety for a defined area of adaptation. Characterization for seed production is also evaluated as part of the testing process.

Genetically Identifying Alfalfa Varieties

In addition to phenotypic observations, a plant can also be identified by its genotype. The genotype of a plant can be characterized through a molecular marker profile. Molecular marker profiling can be used at least to identify plants of the same variety or a related variety, to identify plants and plant parts which are genetically superior as a result of an event comprising a backcross conversion, transgene, or genetic sterility factor, or to determine or validate a pedigree. Such molecular marker profiling can be accomplished by using a variety of techniques including, but not limited to, restriction fragment length polymorphism (RFLP), amplified fragment length polymorphism (AFLP), sequence-tagged sites (STS), randomly amplified polymorphic DNA (RAPD), arbitrarily primed polymerase chain reaction (AP-PCR), DNA amplification fingerprinting (DAF), sequence characterized amplified regions (SCARs), variable number tandem repeat (VNTR), short tandem repeat (STR), single feature polymorphism (SFP), simple sequence length polymorphism (SSLP), restriction site associated DNA, allozymes, isozyme markers, single nucleotide polymorphisms (SNPs), or simple sequence repeat (SSR) markers, also known as microsatellites (Gupta et al., 1999; Korzun et al., 2001). Various types of marker platforms, for example, can be used to identify individual varieties developed from specific parent varieties, as well as cells, or other plant parts thereof. Specific to alfalfa, see, A Saturated Genetic Linkage Map of Autotetraploid Alfalfa (*Medicago sativa* L.) Developed Using Genotyping-by-Sequencing Is Highly Syntenous with the *Medicago truncatula* Genome, G3 (Bethesda). 2014 October; 4(10): 1971-1979; Development of an Alfalfa SNP Array and Its Use to Evaluate Patterns of Population Structure and Linkage Disequilibrium. *PLoS ONE*. 9(1): e84329. https://doi.org/10.1371/journal.pone.0084329; and Construction of an improved linkage map of diploid alfalfa (*Medicago sativa*). *Theor. Appl. Genet.* 100(5):641-657 (March 2000), which are incorporated by reference for this purpose.

In some examples, one or more markers may be used to characterize and/or evaluate an alfalfa variety. Particular markers used for these purposes are not limited to any particular set of markers, but are envisioned to include any type of marker and marker profile that provides a means for distinguishing varieties. One method of comparison may be to use only homozygous loci, i.e., nulliplex or quadriplex loci, for alfalfa variety 412A122. PCR and next-generation sequencing methodologies to identify and assay these and other markers are disclosed in, for example, A Saturated Genetic Linkage Map of Autotetraploid Alfalfa (*Medicago sativa* L.) Developed Using Genotyping-by-Sequencing Is Highly Syntenous with the *Medicago truncatula* Genome, G3 (Bethesda). 2014 October; 4(10): 1971-1979; Development of an Alfalfa SNP Array and Its Use to Evaluate Patterns of Population Structure and Linkage Disequilibrium. *PLoS ONE*. 9(1): e84329. https://doi.org/10.1371/journal.pone.0084329; Construction of an improved linkage map of diploid alfalfa (*Medicago sativa*), Theor. Appl. Genet. 100(5):641-657 (March 2000); and Isolation of a full-length mitotic cyclin cDNA clone CycIIIMs from *Medicago sativa*: Chromosomal mapping and expression, *Plant Mol. Biol.* 27(6):1059-1070 (1995). In addition to being used for identification of alfalfa variety 412A122, as well as plant parts and plant cells of alfalfa variety 412A122, a genetic profile may be used to identify an alfalfa plant produced through the use of alfalfa variety 412A122 or to verify the pedigree of progeny plants or a variety produced through the use of alfalfa variety 412A122. A genetic marker profile may also be useful in marker-assisted selection or backcrossing.

In an embodiment, the present invention provides an alfalfa variety characterized by the molecular and physiological data obtained from a representative sample of said variety deposited with the Provasoli-Guillard National Center for Marine Algae and Microbiota (NCMA). Thus, plants, seeds, or parts thereof, having all of the morphological and physiological characteristics of alfalfa variety 412A122 are provided.

In some examples, a plant, a plant part, or a seed of alfalfa variety 412A122 may be characterized by producing a molecular profile. A molecular profile may include, but is not limited to, one or more genotypic and/or phenotypic profile(s). A genotypic profile may include, but is not limited to, a marker profile, such as a genetic map, a linkage map, a trait maker profile, a SNP profile, an SSR profile, a genome-wide marker profile, a haplotype, or the like. A molecular profile may also be a nucleic acid sequence profile, and/or a physical map. A phenotypic profile may include, but is not limited to, a protein expression profile, a metabolic profile, an mRNA expression profile, and the like.

One means of generating genetic marker profiles is to assay SNPs that are known in the art. Hundreds of thousands of SNPs are known in alfalfa, see Development of an Alfalfa SNP Array and Its Use to Evaluate Patterns of Population Structure and Linkage Disequilibrium. *PLoS ONE*. 9(1): e84329. https://doi.org/10.1371/journal.pone.0084329. A marker system based on SNPs can be highly informative in linkage analysis relative to other marker systems, in that multiple alleles may be present. Another advantage is that SNPs can be detected through use of strategically designed primers, probes, or other specially designed hybridization molecules, which eliminates the need to perform labor-intensive Southern blots. Further, many SNP detection methods are easily scalable and therefore can easily integrate into high-throughput analysis platforms such as microarray and next-generation sequencing technologies. High density microarray platforms, for example, are capable of analyzing hundreds of thousands SNPs on a single microarray chip.

A genotypic profile of alfalfa variety 412A122 can be used to identify a plant or population of plants comprising variety 412A122 as a parent, because such plants will comprise the same allelic profile as alfalfa variety 412A122 at an expected frequency by Mendelian inheritance. In addition, plants and plant parts substantially benefiting from the use of alfalfa variety 412A122 in their development, such as alfalfa variety 412A122 comprising a backcross conversion, transgene, or genetic sterility factor, may be identified by having a molecular marker profile with a high percent identity to alfalfa variety 412A122.

A genotypic profile of alfalfa variety 412A122 also can be used to identify essentially derived varieties and other progeny varieties developed from the use of alfalfa variety 412A122, as well as cells and other plant parts thereof. Plants of the invention include any plant having at least 90%, 91%, 92%, 93%, 94%, 95%, 96%, 97%, 98%, 99%, 99.5%, or 99.9% of the markers in the genotypic profile, and that retain 90%, 91%, 92%, 93%, 94%, 95%, 96%, 97%, 98%, 99%, 99.5%, or 99.9% of the morphological and physiological characteristics of alfalfa variety 412A122 when grown under the same conditions. Such plants may be developed using markers well known in the art. Progeny plants and plant parts produced using alfalfa variety 412A122 may be identified by any means known in the art that is indicative or consistent with the variety. For example, progeny plants and plant parts produced using alfalfa variety 412A122 may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% genetic contribution from alfalfa variety 412A122 by percent identity or percent similarity, or such plants may be identified by statistical genetic parameters such as, but not limited to, allele frequency and fixation index ($F_{ST}$). Such progeny may be further characterized as being within a pedigree distance of alfalfa variety 412A122, such as within 1, 2, 3, 4, or 5 or less cross-pollinations to an alfalfa plant other than alfalfa variety 412A122, or a plant that has alfalfa variety 412A122 as a progenitor. Unique molecular profiles may be identified with other next-generation sequencing tools, such as SNP discovery or haplotype analysis.

Any time the alfalfa variety 412A122 is crossed with a different plant or population, $F_1$ alfalfa progeny is produced. The $F_1$ progeny is produced regardless of characteristics of the parental varieties. As such, an $F_1$ alfalfa plant may be produced by crossing a plant of alfalfa variety 412A122 with any second alfalfa plant. The second alfalfa plant may be genetically homogeneous (e.g., inbred) or may itself be a hybrid. Therefore, any $F_1$ alfalfa plant produced by crossing a plant of alfalfa variety 412A122 with a second alfalfa plant is a part of the present invention.

Further Embodiments of the Invention

In certain aspects of the invention, plants of alfalfa variety 412A122 are modified to include at least a first heritable trait. Such plants may, in one embodiment, be developed by a plant breeding technique called backcrossing, wherein essentially all of the morphological and physiological characteristics of a variety are recovered in addition to a genetic locus, or small number of loci, transferred into the plant via the backcrossing technique. By essentially all of the morphological and physiological characteristics, it is meant that the characteristics of a plant are recovered that are otherwise present when compared in the same environment, other than occasional variant traits that might arise during backcrossing or direct introgression of a transgene. It is understood that a locus introduced by backcrossing may or may not be transgenic in origin, and thus the term backcrossing specifically includes backcrossing to introduce loci that were created by genetic transformation.

In a typical backcross protocol, the original variety of interest (the recurrent parent) is crossed to a second variety (the non-recurrent or donor parent) that carries the specific locus or loci of interest to be transferred. The resulting progeny from this cross are then crossed again to the recurrent parent or a close relative thereof and the process can be repeated until an alfalfa plant is obtained wherein essentially all of the morphological and physiological characteristics of the recurrent parent are recovered in the converted plant, in addition to the transferred locus from the donor parent.

The selection of a suitable recurrent parent is an important step for a successful backcrossing procedure. The goal of a backcross protocol is to alter or substitute a trait or characteristic in the original variety. To accomplish this, a locus of the recurrent parent is modified or substituted with the desired locus from the donor parent, while retaining essentially all of the rest of the genome of the original parent, and therefore the morphological and physiological constitution of the original variety. The choice of the donor parent will depend on the purpose of the backcross. One of the primary purposes is to add a commercially or agronomically significant trait to the plant or variety. The specific backcrossing protocol will depend on the characteristic or trait being altered to determine an appropriate testing protocol. Although backcrossing methods are simplified when the characteristic being transferred is a dominant allele, a recessive allele may also be transferred. If the trait of interest is transferred via a recessive allele, a test of the progeny may be employed to determine if the desired characteristic has been successfully transferred.

The traditional backcross technique can be adjusted to include more than one recurrent parent when breeding plants such as alfalfa, in which homozygosity can result in inbreeding depression, agronomic performance decline, and loss of traits of interest. This type of backcrossing is known as modified backcrossing and employs at least two different recurrent parents to produce a sufficiently heterozygous population with the agronomically significant characteristics of the recurrent parents and the trait or traits of interest from the donor parent. Modified backcrossing may also be used to replace the original recurrent parent with one or more distinct parents to stack different characteristics from each, and therefore providing additional improvement over a single recurrent parent.

Backcrossing techniques can be used to improve many traits that may not normally be selection targets when developing a new alfalfa variety. These traits may or may not be transgenic. Examples of these traits include, but are not limited to, male sterility, herbicide resistance, resistance to bacterial, fungal, or viral disease, insect and pest resistance, restoration of male fertility, enhanced nutritional quality, yield stability, and yield enhancement. These comprise genes generally inherited through the nucleus.

Direct selection may be applied when the locus acts as a dominant trait. An example of a dominant trait is the herbicide resistance trait. For this selection process, progeny plants of the initial cross are sprayed with the herbicide prior to the backcrossing. The spraying eliminates any plants which do not have the selected herbicide resistance characteristic, and only those plants that have the herbicide resistance gene are advanced. This process is then repeated for all additional generations.

Selection of alfalfa plants for breeding is not necessarily dependent on the phenotype of a plant and instead can be based on genetic investigations. For example, one may utilize a suitable genetic marker that is closely associated with a trait of interest. One of these markers may therefore be used to identify the presence or absence of a trait in the progeny of a particular cross, and hence may be used to select progeny for continued breeding. This technique may commonly be referred to as marker assisted selection. Any other type of genetic marker or other assay that is able to identify the relative presence or absence, i.e., dosage, of a trait of interest in a plant may also be useful for breeding purposes. Procedures for marker-assisted selection applicable to the breeding of alfalfa are well known in the art. Such methods will be of particular utility in the case of recessive traits, phenotypes that are not consistently expressed in selection environments, or when conventional assays may be more expensive, time-consuming or otherwise disadvantageous. Genetic markers that could be used in accordance with the invention include, but are not necessarily limited to, Single Nucleotide Polymorphisms (SNPs), Simple Sequence Length Polymorphisms (SSLPs), Sequence Characterized Amplified Regions (SCARs), and Amplified Fragment Length Polymorphisms (AFLPs). Additionally, methods known in the art that generate genetic profiles capable of distinguishing between different genotypes can be used in accordance with the invention and include, but are not necessarily limited to, next-generation sequencing technologies, microarrays, Randomly Amplified Polymorphic DNAs (RAPDs), DNA Amplification Fingerprinting (DAF), and Arbitrary Primed Polymerase Chain Reaction (AP-PCR). Many qualitative characteristics also have a potential use as phenotype-based genetic markers in accordance with this invention.

Many useful traits that can be introduced by backcrossing, as well as directly into a plant, are those that are introduced by genetic transformation techniques. Genetic transformation may be used to insert a selected transgene into the alfalfa variety 412A122 or may, alternatively, be used for the preparation of transgenes which can be introduced by backcrossing. Methods for the transformation of many economically important plants, including alfalfa, are well known to those of skill in the art. Techniques which may be employed to genetically transform alfalfa include, but are not limited to, electroporation, microprojectile bombardment, *Agrobacterium*-mediated transformation and direct DNA uptake by protoplasts. Specific to alfalfa, see, "Efficient *Agrobacterium*-mediated transformation of alfalfa using secondary somatic embryogenic callus," Journal of the Korean Society of Grassland Science 20 (1):13-18 (2000); E. Charles Brummer, "Applying Genomics to Alfalfa Breeding Programs" Crop Sci. 44:1904-1907 (2004); and "Genetic transformation of commercial breeding populations of alfalfa (*Medicago sativa*)" Plant Cell Tissue and Organ Culture 42(2): 129-140 (1995), which are incorporated by reference for this purpose.

To effect transformation by electroporation, one may employ either friable tissues, such as a suspension culture of cells or embryogenic callus, or one may transform immature embryos or other organized tissue directly. In this technique, one would partially degrade the cell walls of the chosen cells by exposing them to pectin-degrading enzymes (pectolyases) or mechanically wound tissues in a controlled manner. Protoplasts may also be employed for electroporation transformation of plants (Bates, *Mol. Biotechnol.*, 2(2):135-145, 1994; Lazzeri, *Methods Mol. Biol.*, 49:95-106, 1995).

Another efficient method for delivering DNA segments to plant cells is microprojectile bombardment. In this method, particles are coated with nucleic acids and delivered into cells by a propelling force. Exemplary particles include those comprised of tungsten, platinum, or gold. For the bombardment, cells in suspension are concentrated on filters or solid culture medium. Alternatively, immature embryos or other target cells may be arranged on solid culture medium. The cells to be bombarded are positioned at an appropriate distance below the microprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target alfalfa cells. The screen disperses the particles so that they are not delivered to the recipient cells in large aggregates. It is believed that a screen intervening between the projectile apparatus and the cells to be bombarded reduces the size of the projectile aggregate and may contribute to a higher frequency of transformation by reducing the damage inflicted on the recipient cells by projectiles that are too large. Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., *Bio. Tech.*, 3(7):637-642, 1985). Moreover, recent technological advances in vectors for *Agrobacterium*-mediated gene transfer have improved the arrangement of genes and cloning sites in the vectors to facilitate the construction of vectors capable of expressing various polypeptide coding genes. Vectors can have convenient multiple-cloning sites (MCS) flanked by a promoter and a polyadenylation site for direct expression of inserted polypeptide coding genes. Other vectors can comprise site-specific recombination sequences, enabling insertion of a desired DNA sequence without the use of restriction enzymes (Curtis et al., *Plant Physiology* 133:462-469, 2003). Additionally, *Agrobacterium* containing both armed and disarmed Ti genes can be used for transformation.

In those plant strains in which *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., *Bio. Tech.*, 3(7):629-635, 1985; U.S. Pat. No. 5,563,055).

Transformation of plant protoplasts also can be achieved using methods based on calcium phosphate precipitation, polyethylene glycol treatment, electroporation, and combinations of these treatments. See, e.g., Potrykus et al., *Mol. Gen. Genet.*, 199(2):169-177, 1985; Omirulleh et al., *Plant Mol. Biol.*, 21(3):415-428, 1993; Fromm et al., *Nature*, 319(6056):791-793, 1986; Uchimiya et al., *Mol. Gen. Genet.*, 204(2):204-207, 1986; Marcotte et al., *Nature*, 335 (6189):454-457, 1988).

Included among various plant transformation techniques are methods permitting the site-specific modification of a plant genome. These modifications can include, but are not limited to, site-specific mutations, deletions, insertions, and replacements of nucleotides. These modifications can be made anywhere within the genome of a plant, for example, in genomic elements, including, among others, coding sequences, regulatory elements, and non-coding DNA sequences. Any number of such modifications can be made and that number of modifications may be made in any order or combination, for example, simultaneously all together or one after another. Such methods may lead to changes in phenotype. The techniques for such modifications are well known in the art and include, for example, use of CRISPR-Cas systems, zinc-finger nucleases (ZFNs), and transcription activator-like effector nucleases (TALENs), among others.

Many hundreds if not thousands of different genes are known and could potentially be introduced into an alfalfa plant according to the invention. Non-limiting examples of particular genes and corresponding phenotypes one may choose to introduce into an alfalfa plant are presented below.

A. Male Sterility

Genetic male sterility is available in alfalfa. Although male sterility is not required for crossing alfalfa plants, it is an efficient means by which to generate alfalfa varieties with increased hybridism, as generation of true-breeding alfalfa varieties is challenging due to alfalfa being highly self-incompatible. Alfalfa male sterility systems have been described in, for example, U.S. Pat. Nos. 6,774,280 and 7,067,721, the disclosures of which are each specifically incorporated herein by reference in their entirety.

In one embodiment of the present invention, plants of alfalfa variety 412A122 or plants derived therefrom may be incorporated into a breeding scheme to produce progeny with increased hybridism such as breeding with cytoplasmic male sterile lines. The present invention therefore provides a method of obtaining alfalfa populations with high hybridism using cytoplasmic male sterile (CMS), maintainer, and pollenizer (male-fertile) alfalfa populations. The cells of the CMS alfalfa plants contain sterile cytoplasm and a non-restorer gene. The cells of a maintainer alfalfa plants contains normal cytoplasm and the non-restorer gene. The pollenizer alfalfa line is fertile, displaying both male and female parts.

The CMS and maintainer plants can be crossed, and the resultant seed produced by the CMS parents would be hybrid and male sterile. These hybrid, male sterile seed can then be randomly bulked with pollenizer seed preferably at a ratio of 4:1, respectively. This bulked seed can then be grown and those plants intercrossed. The resulting seed from such a cross should have at least 75% hybridity, i.e., at least 75% of the seeds are genetically distinct from both their male and female parents.

Male sterile populations may be identified by evaluating pollen production using the Pollen Production Index (P.P.I.), which recognizes the four distinct classes shown in Table 15.

TABLE 15

Pollen Product Index (P.P.I.) Classes.

| Class | P.P.I. | Characteristics |
| --- | --- | --- |
| Male Sterile Plant (MS) | 0 | Visible pollen can be observed with the naked eye when flower is tripped with a black knife blade. |
| Partial Male Sterile Plant (PMS) | 0.1 | A trace of pollen is found with the naked eye when flower is tripped with a black knife blade. |
| Partial Fertile Plant (PF) | 0.6 | Less than a normal amount of pollen can be observed with the naked eye when flower is tripped with a black knife blade. |
| Fertile Plant (F) | 1.0 | Normal amounts of pollen can be observed when flower is tripped with a black knife blade. |

B. Herbicide Resistance

Numerous herbicide resistance genes are known and may be employed with the invention. A non-limiting example is a gene conferring resistance to a herbicide that inhibits the growing point or meristem such as imidazolinone or sulfonylurea herbicides. As imidazolinone and sulfonylurea herbicides are acetolactate synthase (ALS)-inhibiting herbicides that prevent the formation of branched chain amino acids, exemplary genes in this category code for ALS and AHAS enzymes as described, for example, by Lee et al., *EMBO J.*, 7:1241, 1988; Gleen et al., *Plant Molec. Biology*, 18:1185, 1992; and Miki et al., *Theor. Appl. Genet.*, 80:449, 1990. As a non-limiting example, a gene may be employed to confer resistance to the exemplary sulfonylurea herbicide nicosulfuron.

Resistance genes for glyphosate (resistance conferred by mutant 5-enolpyruvylshikimate-3-phosphate synthase (EPSPS) and aroA genes, respectively) and other phosphono compounds such as glufosinate (phosphinothricin acetyltransferase (PAT) and *Streptomyces hygroscopicus* phosphinothricin acetyltransferase (bar) genes) may also be used. See, for example, U.S. Pat. No. 4,940,835 to Shah et al., which discloses the nucleotide sequence of a form of EPSPS that can confer glyphosate resistance. Non-limiting examples of EPSPS transformation events conferring glyphosate resistance are provided by U.S. Pat. Nos. 7,566,817; 8,124,848; and 9,068,196. The J-101 event disclosed in U.S. Pat. No. 7,566,817 is beneficial in conferring glyphosate tolerance in alfalfa.

A DNA molecule encoding a mutant aroA gene can be obtained under ATCC Accession No. 39256, and the nucleotide sequence of the mutant gene is disclosed in U.S. Pat. No. 4,769,061 to Comai. A hygromycin B phosphotransferase gene from *E. coli* that confers resistance to glyphosate in tobacco callus and plants is described in Penaloza-Vazquez et al., *Plant Cell Reports*, 14:482, 1995. European Patent Application Publication No. EP0333033 to Kumada et al., and U.S. Pat. No. 4,975,374 to Goodman et al., disclose nucleotide sequences of glutamine synthetase genes that confer resistance to herbicides such as L-phosphinothricin. The nucleotide sequence of a phosphinothricin acetyltransferase gene is provided in European Patent Application Publication No. EP0242246 to Leemans et al. DeGreef et al. (*Biotechnology*, 7:61, 1989) describe the production of transgenic plants that express chimeric bar genes coding for phosphinothricin acetyl transferase activity. Exemplary genes conferring resistance to a phenoxy class herbicide haloxyfop and a cyclohexanedione class herbicide sethoxydim are the Acct-S1, Acct-S2 and Acct-S3 genes described by Marshall et al., (*Theor. Appl. Genet.*, 83:435, 1992). As a non-limiting example, a gene may confer resistance to other exemplary phenoxy class herbicides that include, but are not limited to, quizalofop-p-ethyl and 2,4-dichlorophenoxyacetic acid (2,4-D).

Genes are also known that confer resistance to herbicides that inhibit photosynthesis such as, for example, triazine herbicides (psbA and gs+ genes) and benzonitrile herbicides (nitrilase gene). As a non-limiting example, a gene may confer resistance to the exemplary benzonitrile herbicide bromoxynil. Przibila et al. (*Plant Cell*, 3:169, 1991) describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441, and 67442. Cloning and expression of DNA coding for a glutathione S-transferase is described by Hayes et al. (*Biochem. J.*, 285:173, 1992). 4-hydroxyphenylpyruvate dioxygenase (HPPD) is a target of the HPPD-inhibiting herbicides, which deplete plant plastoquinone and vitamin E pools. Rippert et al. (*Plant Physiol.*, 134:92, 2004) describes an HPPD-inhibitor resistant tobacco plant that was transformed with a yeast-derived prephenate dehydrogenase (PDH) gene. Protoporphyrinogen oxidase (PPO) is the target of the PPO-inhibitor class of herbicides; a PPO-inhibitor resistant PPO gene was recently identified in *Amaranthus tuberculatus* (Patzoldt et al., *PNAS*, 103(33):12329, 2006). The herbicide methyl viologen inhibits $CO_2$ assimilation. Foyer et al. (*Plant Physiol.*, 109:1047, 1995) describe a plant overexpressing glutathione reductase (GR) that is resistant to methyl viologen treatment.

Siminszky (*Phytochemistry Reviews*, 5:445, 2006) describes plant cytochrome P450-mediated detoxification of multiple, chemically unrelated classes of herbicides. Modified bacterial genes have been successfully demonstrated to confer resistance to atrazine, a herbicide that binds to the plastoquinone-binding membrane protein $Q_B$ in photosystem II to inhibit electron transport. See, for example, studies by Cheung et al. (*PNAS*, 85:391, 1988), describing tobacco plants expressing the chloroplast psbA gene from an atrazine-resistant biotype of *Amaranthus hybridus* fused to the regulatory sequences of a nuclear gene, and Wang et al. (*Plant Biotech. J.*, 3:475, 2005), describing transgenic alfalfa, *Arabidopsis*, and tobacco plants expressing the atzA gene from *Pseudomonas* sp. that were able to detoxify atrazine.

Bayley et al. (*Theor. Appl. Genet.*, 83:645, 1992) describe the creation of 2,4-D-resistant transgenic tobacco and cotton plants using the 2,4-D monooxygenase gene tfdA from *Alcaligenes eutrophus* plasmid pJP5. U.S. Patent Application Publication No. 20030135879 describes the isolation of a gene for dicamba monooxygenase (DMO) from *Psueodmonas maltophilia* that is involved in the conversion of dicamba to a non-toxic 3,6-dichlorosalicylic acid and thus may be used for producing plants tolerant to this herbicide.

Other examples of herbicide resistance have been described, for instance, in U.S. Pat. Nos. 6,803,501; 6,448,476; 6,248,876; 6,225,114; 6,107,549; 5,866,775; 5,804,425; 5,633,435; 5,463,175.

C. Disease and Pest Resistance

Plant defenses are often activated by specific interaction between the product of a disease resistance gene (R) in the plant and the product of a corresponding avirulence (Avr) gene in the pathogen. A plant line can be transformed with a cloned resistance gene to engineer plants that are resistant to specific pathogen strains. See, for example Jones et al. (*Science*, 266:789-793, 1994) (cloning of the tomato Cf-9 gene for resistance to *Cladosporium flavum*); Martin et al. (*Science*, 262:1432-1436, 1993) (tomato Pto gene for resistance to *Pseudomonas syringae* pv. tomato); and Mindrinos et al. (*Cell*, 78(6):1089-1099, 1994) (*Arabidopsis* RPS2 gene for resistance to *Pseudomonas syringae*).

A viral-invasive protein or a complex toxin derived therefrom may also be used for viral disease resistance. For example, the accumulation of viral coat proteins in transformed plant cells imparts resistance to viral infection and/or disease development effected by the virus from which the coat protein gene is derived and related viruses. See Beachy et al. (*Ann. Rev. Phytopathol.*, 28:451, 1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus.

A virus-specific antibody may also be used. See, for example, Tavladoraki et al. (*Nature*, 366:469-472, 1993), who show that transgenic plants expressing recombinant antibody genes are protected from virus attack. Virus resistance has also been described in, for example, U.S. Pat. Nos. 6,617,496; 6,608,241; 6,015,940; 6,013,864; 5,850,023 and 5,304,730. Additional means of inducing whole-plant resistance to a pathogen include modulation of the systemic acquired resistance (SAR) or pathogenesis related (PR) genes, for example genes homologous to the *Arabidopsis thaliana* NIM1/NPR1/SAI1, and/or by increasing salicylic acid production (Ryals et al., *Plant Cell*, 8:1809-1819, 1996).

Logemann et al. (*Biotechnology*, 10:305-308, 1992), for example, disclose transgenic plants expressing a barley ribosome-inactivating gene that have an increased resistance to fungal disease. Plant defensins may be used to provide resistance to fungal pathogens (Thomma et al., *Planta*, 216:193-202, 2002). Other examples of fungal disease resistance are provided in U.S. Pat. Nos. 6,653,280; 6,573,361; 6,506,962; 6,316,407; 6,215,048; 5,516,671; 5,773,696; 6,121,436; and 6,316,407.

Nematode resistance has been described in, for example, U.S. Pat. No. 6,228,992, and bacterial disease resistance has been described in, for example, U.S. Pat. No. 5,516,671.

D. Insect Resistance

One example of an insect resistance gene includes a *Bacillus thuringiensis* protein, a derivative thereof, or a synthetic polypeptide modeled thereon. See, for example, Geiser et al. (*Gene*, 48(1):109-118, 1986), who disclose the cloning and nucleotide sequence of a *Bacillus thuringiensis* δ-endotoxin gene. Moreover, DNA molecules encoding δ-endotoxin genes are deposited under ATCC Accession Nos. 40098, 67136, 31995, and 31998. Another example is a lectin. See, for example, Van Damme et al., (*Plant Molec. Biol.*, 24:825-830, 1994), who disclose the nucleotide sequences of several *Clivia miniata* mannose-binding lectin genes. A vitamin-binding protein may also be used, such as, for example, avidin. See PCT Application No. US93/06487, the contents of which are hereby incorporated by reference. This application teaches the use of avidin and avidin homologues as larvicides against insect pests.

Yet another insect resistance gene is an enzyme inhibitor, for example, protease, proteinase, or amylase inhibitors. See, for example, Abe et al. (*J. Biol. Chem.*, 262:16793-16797, 1987) describing the nucleotide sequence of a rice cysteine proteinase inhibitor; Linthorst et al. (*Plant Molec. Biol.*, 21:985-992, 1993) describing the nucleotide sequence of a cDNA encoding tobacco proteinase inhibitor I; and Sumitani et al. (*Biosci. Biotech. Biochem.*, 57:1243-1248, 1993) describing the nucleotide sequence of a *Streptomyces nitrosporeus* α-amylase inhibitor.

An insect-specific hormone or pheromone may also be used. See, for example, the disclosure by Hammock et al. (*Nature*, 344:458-461, 1990) of baculovirus expression of cloned juvenile hormone esterase, an inactivator of juvenile hormone; Gade and Goldsworthy (*Eds. Physiological System in Insects*, Elsevier Academic Press, Burlington, Mass., 2007), describing allostatins and their potential use in pest control; and Palli et al. (*Vitam. Horm.*, 73:59-100, 2005), disclosing use of ecdysteroid and ecdysteroid receptor in agriculture. The diuretic hormone receptor (DHR) was identified in Price et al. (*Insect Mol. Biol.*, 13:469-480, 2004) as another potential candidate target of insecticides.

Still other examples include an insect-specific antibody or an immunotoxin derived therefrom and a developmental-arrestive protein. See Taylor et al. (Seventh Int'l Symposium on Molecular Plant-Microbe Interactions, Edinburgh, Scotland, Abstract W97, 1994), who described enzymatic inactivation in transgenic tobacco via production of single-chain antibody fragments. Numerous other examples of insect resistance have been described. See, for example, U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658; 5,880,275; 5,763,245; and 5,763,241.

E. Modified Fatty Acid, Phytate, and Carbohydrate Metabolism

Genes may be used conferring modified fatty acid metabolism. For example, stearyl-ACP desaturase genes may be used, see Knutzon et al. (*Proc. Natl. Acad. Sci. USA*, 89:2624-2628, 1992). Various fatty acid desaturases have also been described. McDonough et al. describe a *Saccharomyces cerevisiae* OLE1 gene encoding Δ9-fatty acid desaturase, an enzyme which forms the monounsaturated palmitoleic (16:1) and oleic (18:1) fatty acids from palmitoyl (16:0) or stearoyl (18:0) CoA (*J. Biol. Chem.*, 267(9): 5931-5936, 1992). Fox et al. describe a gene encoding a stearoyl-acyl carrier protein Δ9-desaturase from castor (*Proc. Natl. Acad. Sci. USA*, 90(6):2486-2490, 1993). Reddy et al. describe Δ6- and Δ12-desaturases from the cyanobacteria *Synechocystis* responsible for the conversion of linoleic acid (18:2) to gamma-linolenic acid (18:3 gamma) (*Plant Mol. Biol.*, 22(2):293-300, 1993). Arondel et al. describe a gene from *Arabidopsis thaliana* that encodes an omega-3 desaturase (*Science*, 258(5086):1353-1355, 1992). Plant Δ9-desaturases as well as soybean and *Brassica* Δ15-desaturases have also been described, see PCT Application Publication No. WO 91/13972 and European Patent Application Publication No. EP0616644, respectively. U.S. Pat. No. 7,622,632 describes fungal Δ15-desaturases and their use in plants. European Patent Application Publication No. EP1656449 describes Δ6-desaturases from *Primula*.

Modified oil production is disclosed in, for example, U.S. Pat. Nos. 6,444,876; 6,426,447; and 6,380,462. High oil production is disclosed in, for example, U.S. Pat. Nos. 6,495,739; 5,608,149; 6,483,008; and 6,476,295. Modified fatty acid content is disclosed in, for example, U.S. Pat. Nos. 6,828,475; 6,822,141; 6,770,465; 6,706,950; 6,660,849; 6,596,538; 6,589,767; 6,537,750; 6,489,461 and 6,459,018.

Phytate metabolism may also be modified by introduction of a phytase-encoding gene to enhance breakdown of phytate, adding more free phosphate to the transformed plant. For example, see Van Hartingsveldt et al. (*Gene*, 127:87-94, 1993), for a disclosure of the nucleotide sequence of an *Aspergillus niger* phytase gene, and see Raboy et al. (*Plant Physiol.*, 124(1):355-368, 2000) for the disclosure of low phytic acid mutant maize alleles lpa1-1 and lpa2-1.

A number of genes are known that may be used to alter carbohydrate metabolism. For example, plants may be transformed with a gene coding for an enzyme that alters the branching pattern of starch. For example, Shiroza et al. (*J. Bacteriol.*, 170:810-816, 1988) describe a nucleotide sequence of the *Streptococcus mutans* fructosyltransferase gene; Steinmetz et al. (*Mol. Gen. Genet.*, 20:220-228, 1985) describe a nucleotide sequence of the *Bacillus subtilis* levansucrase gene; Pen et al. (*Biotechnology*, 10:292-296, 1992) describe production of transgenic plants that express *Bacillus licheniformis* α-amylase; Elliot et al. (*Plant Molec. Biol.*, 21:515-524, 1993) describe nucleotide sequences of tomato invertase genes; Sergaard et al. (*J. Biol. Chem.*, 268:22480, 1993) describe site-directed mutagenesis of a barley α-amylase gene; and Fisher et al. (*Plant Physiol.*, 102:1045-1046, 1993) describe maize endosperm starch branching enzyme II. The Z10 gene encoding a 10 kD zein storage protein from maize may also be used to alter the quantities of 10 kD zein in the cells relative to other components (Kirihara et al., *Gene*, 71(2):359-370, 1988).

F. Resistance to Abiotic Stress

Abiotic stress includes dehydration or other osmotic stress, salinity, high or low light intensity, high or low temperatures, submergence, exposure to heavy metals, and oxidative stress. Delta-pyrroline-5-carboxylate synthetase (P5CS) from mothbean has been used to provide protection against general osmotic stress. Mannitol-1-phosphate dehydrogenase (mt1D) from *E. coli* has been used to provide protection against drought and salinity. Choline oxidase (codA from *Arthrobactor globiformis*) can protect against cold and salt. *E. coli* choline dehydrogenase (betA) provides protection against salt. Additional protection from cold can be provided by omega-3-fatty acid desaturase (fad7) from *Arabidopsis thaliana*. Trehalose-6-phosphate synthase and levan sucrase (SacB) from yeast and *Bacillus subtilis*, respectively, can provide protection against drought (summarized from Annex II Genetic Engineering for Abiotic Stress Tolerance in Plants, Consultative Group On International *Agricultural Research* Technical Advisory Committee). Overexpression of superoxide dismutase can be used to protect against superoxides, see U.S. Pat. No. 5,538,878.

G. Additional Traits

Additional traits can be introduced into alfalfa variety 412A122. A non-limiting example of such a trait is a coding sequence which decreases RNA and/or protein levels. The decreased RNA and/or protein levels may be achieved through RNAi methods, such as those described in U.S. Pat. No. 6,506,559.

Another trait that may find use with alfalfa variety 412A122 is a sequence which allows for site-specific recombination. Examples of such sequences include the FRT sequence used with the FLP recombinase (Zhu and Sadowski, *J. Biol. Chem.*, 270:23044-23054, 1995) and the LOX sequence used with CRE recombinase (Sauer, *Mol. Cell. Biol.*, 7:2087-2096, 1987). The recombinase genes can be encoded at any location within the genome of the alfalfa plant and are active in the hemizygous state.

In certain embodiments alfalfa plants may be made more tolerant to or more easily transformed with *Agrobacterium tumefaciens*. For example, expression of p53 and iap, two baculovirus cell-death suppressor genes, inhibited tissue necrosis and DNA cleavage. Additional targets may include plant-encoded proteins that interact with the *Agrobacterium* Vir genes; enzymes involved in plant cell wall formation; and histones, histone acetyltransferases and histone deacetylases (reviewed in Gelvin, *Microbiology & Mol. Biol. Reviews*, 67:16-37, 2003).

In addition to the modification of oil, fatty acid, or phytate content described above, certain embodiments may modify the amounts or levels of other compounds. For example, the amount or composition of antioxidants can be altered. See, for example, U.S. Pat. Nos. 6,787,618 and 7,154,029 and International Patent Application Publication No. WO 00/68393, which disclose the manipulation of antioxidant levels, and International Patent Application Publication No. WO 03/082899, which discloses the manipulation of an antioxidant biosynthetic pathway. In other embodiments the level of lignin may altered. See, for example, U.S. Pat. Nos. 9,670,498; 9,701,976; and 9,854,778, which disclose event KK179-2. The KK179-2 event is beneficial in reducing lignin in alfalfa plants. The event encodes dsRNA that suppress endogenous S-adenosyl-L-methionine: transcaffeoyl CoA 3-O-methyltransferase levels, which consequently suppresses lignin production.

In certain embodiments alfalfa plants may be modified to augment their nitrogen fixation capacity. In specific embodiments, this may comprise a genetic modification that augments the intrinsic physiology or morphology of alfalfa that enables or facilitates nitrogen fixation. In other embodiments, modifications may augment the interactions, including biological interactions, between an alfalfa plant and nitrogen fixing bacteria such as, for example, *Sinorhizobium meliloti*.

Additionally, seed amino acid content may be manipulated. U.S. Pat. No. 5,850,016 and International Patent Application Publication No. WO 99/40209 disclose the alteration of the amino acid compositions of seeds. U.S. Pat. Nos. 6,080,913 and 6,127,600 disclose methods of increasing accumulation of essential amino acids in seeds.

U.S. Pat. No. 5,559,223 describes synthetic storage proteins of which the levels of essential amino acids can be manipulated. International Patent Application Publication No. WO 99/29882 discloses methods for altering amino acid content of proteins. International Patent Application Publication No. WO 98/20133 describes proteins with enhanced levels of essential amino acids. International Patent Application Publication No. WO 98/56935 and U.S. Pat. Nos. 6,346,403; 6,441,274; and 6,664,445 disclose plant amino acid biosynthetic enzymes. International Patent Application Publication No. WO 98/45458 describes synthetic seed proteins having a higher percentage of essential amino acids than wild-type.

U.S. Pat. No. 5,633,436 discloses plants comprising a higher content of sulfur-containing amino acids; U.S. Pat. No. 5,885,801 discloses plants comprising a high threonine content; U.S. Pat. Nos. 5,885,802 and 5,912,414 disclose plants comprising a high methionine content; U.S. Pat. No. 5,990,389 discloses plants comprising a high lysine content; U.S. Pat. No. 6,459,019 discloses plants comprising an increased lysine and threonine content; International Patent Application Publication No. WO 98/42831 discloses plants comprising a high lysine content; International Patent Application Publication No. WO 96/01905 discloses plants comprising a high threonine content; and International Patent Application Publication No. WO 95/15392 discloses plants comprising a high lysine content.

Tissue Cultures and In Vitro Regeneration of Alfalfa Plants

A further aspect of the invention relates to tissue cultures of alfalfa variety 412A122. As used herein, the term "tissue culture" indicates a composition comprising isolated cells of the same or a different type or a collection of such cells organized into parts of a plant. Exemplary types of tissue cultures are protoplasts, calli, and plant cells that are intact in plants or parts of plants, such as embryos, pollen, flowers, leaves, roots, root tips, anthers, and the like. In one embodiment, the tissue culture comprises embryos, protoplasts, meristematic cells, pollen, leaves, or anthers.

Exemplary procedures for preparing tissue cultures of regenerable alfalfa cells and regenerating alfalfa plants therefrom are disclosed in U.S. Pat. No. 5,324,646, which is specifically incorporated herein by reference in its entirety. Tissue culture of alfalfa is further described in Saunders, J. W. and Bingham, E. T., *Production of alfalfa plants from callus tissue*, Crop Sci 12:804-808 (1971), and incorporated herein by reference.

An important ability of a tissue culture is the capability to regenerate fertile plants. This allows, for example, transformation of the tissue culture cells followed by regeneration of transgenic plants. For transformation to be efficient and successful, DNA must be introduced into cells that give rise to plants or germ-line tissue.

Plants typically are regenerated via two distinct processes: shoot morphogenesis and somatic embryogenesis. Shoot morphogenesis is the process of shoot meristem organization and development. Shoots grow out from a source tissue and are excised and rooted to obtain an intact plant. During somatic embryogenesis, an embryo (similar to the zygotic embryo), containing both shoot and root axes, is formed from somatic plant tissue. An intact plant rather than a rooted shoot results from the germination of the somatic embryo.

Shoot morphogenesis and somatic embryogenesis are different processes and the specific route of regeneration is primarily dependent on the explant source and media used for tissue culture manipulations. While the systems are different, both systems show variety-specific responses in which some lines are more responsive to tissue culture manipulations than others. A line that is highly responsive in shoot morphogenesis may not generate many somatic embryos. Lines that produce large numbers of embryos during an 'induction' step may not give rise to rapidly-growing proliferative cultures. Therefore, it may be desired to optimize tissue culture conditions for each alfalfa line. These optimizations may readily be carried out by one of skill in the art of tissue culture through small-scale culture studies. In addition to line-specific responses, proliferative cultures can be observed with both shoot morphogenesis and somatic embryogenesis. Proliferation is beneficial for both systems as it allows a single, transformed cell to multiply to the point that it will contribute to germ-line tissue.

Embryogenic cultures can also be used successfully for regeneration, including regeneration of transgenic plants, if the origin of the embryos is recognized and the biological limitations of proliferative embryogenic cultures are understood. Biological limitations include the difficulty in developing proliferative embryogenic cultures and reduced fertility problems (culture-induced variation) associated with plants regenerated from long-term proliferative embryogenic cultures. Some of these problems are accentuated in prolonged cultures. The use of more recently cultured cells may decrease or eliminate such problems.

Definitions

In the description and tables, a number of terms are used. In order to provide a clear and consistent understanding of the specification and claims, the following definitions are provided:

A: When used in conjunction with the word "comprising" or other open language in the claims, the words "a" and "an" denote "one or more."

About: Refers to embodiments or values that include the standard deviation of the mean for a given item being measured.

Acid-Detergent Fiber (ADF): A measurement that approximates the amount of cellulose fiber and ash present in a feed. Forages with high ADF values are less digestible than forages with low ADF values, and therefore provide fewer nutrients to the animal through digestion. Because of this relationship, ADF serves as an estimate of digestibility and can be used by nutritionists to predict the energy that will be available from a forage.

Allele: Any of one or more alternative forms of a locus. In a diploid cell or organism, the two alleles of a given locus occupy corresponding loci on a pair of homologous chromosomes.

AOSCA: The abbreviation for the Association of Official Seed Certifying Agencies.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Check Cultivars: A single set of check cultivars that represent fall dormancy classes (FDC) 1 to 11. These check cultivars have been selected to maintain the intended relationship between the original set of nine check cultivars (Standard Tests, March 1991, updated in 1998) and to have minimal variation across environments. The actual fall dormancy rating (FDR) is based on the average University of California regression. The Certified Alfalfa Seed Council Class that each check cultivar represents is listed below in Table 16.

Crossing: The mating of two plants.

Cross-pollination: Fertilization by the union of two gametes from different plants.

Crude Protein (CP): A measurement in which the total nitrogen concentration of a forage is multiplied by 6.25. This technique measures not only the nitrogen present in true proteins, but also that present in non-protein forms such as ammonia, urea and nitrate. Because most of the non-protein forms of nitrogen are converted to true protein by the rumen microorganisms, CP is considered by nutritionists to provide an accurate measure of the protein that will be available to ruminant animals from a given forage.

Dietary Dry Matter (DM): The matter e.g., protein, fiber, fat, minerals, etc., within a sample of alfalfa excluding water. It is one metric by which yield may be calculated.

Emasculate: The removal of plant male sex organs or the deactivation of the organs with a cytoplasmic or nuclear genetic factor or a chemical agent conferring male sterility.

Enzymes: Molecules which can act as catalysts in biological reactions.

$F_1$ Hybrid: The first filial generation of progeny derived from a cross between two plants of different genotypes.

Fall Dormancy (Dormancy or FD): Most alfalfa plants go dormant in the fall in preparation for winter. This is characterized by a reduction in growth rates and metabolism as well as the storage of carbohydrate in the root system of the plants. The onset of dormancy is genotype dependent and is triggered by a combination of day length and temperature. The dormancy response of alfalfa genotypes can be quantified by measuring plant height in autumn relative to a set of standard check varieties.

Fall dormancy test: The test requires that plants are cut off in early September with plant height measured in early-mid October. Early fall dormant types show very little regrowth after the September clipping; whereas, later fall dormant types demonstrate substantial growth. The fall dormancy groups are numbered 1 to 11, in which Dormancy Group 1 is most dormant and suited for cold climates, i.e., these varieties would stop growing and go dormant over winter, and Dormancy Groups 7-11 are very non-dormant and would continue to regrow after fall cuttings. Dormancy groups 7-11 are suited for warm to very hot climates, and would have relatively high winter activity. The NA&MLVRB recognizes standard or check varieties for Dormancy Groups 1-11. The check varieties for the various fall dormancy ratings/Dormancy Groups (corresponding to the rating scale used by the Certified Alfalfa Seed Council (CASC)) are listed in Table 16.

Genetic Dosage: The number of copies of a particular gene, allele, locus, or transgene that are present in the genome of an organism. Alfalfa as an autotetraploid may contain genes, alleles, loci, or transgenes in at least simplex, duplex, triplex, or quadraplex dosages.

Genetic Complement: An aggregate of nucleotide sequences, the expression of which sequences defines the phenotype in alfalfa plants, or components of plants including cells or tissue.

Genotype: The genetic constitution of a cell or organism.

Haploid: A cell or organism having one set of the two sets of chromosomes in a diploid.

Haplotype Analysis: A genetic profile of a particular organism in which genetic markers, typically SNPs, and linkage maps are used to identify the parent and/or earlier ancestors from which one or more genetic loci were inherited.

Isozymes: Detectable variants of an enzyme, the variants catalyzing the same reaction(s) but differing from each other, e.g., in primary structure and/or electrophoretic mobility. The differences between isozymes are under single gene, codominant control. Consequently, electrophoretic separation to produce band patterns can be equated to different alleles at the DNA level. Structural differences that do not alter charge cannot be detected by this method.

In Vitro True Digestibility (IVTD): A measurement of digestibility utilizing actual rumen microorganisms. Although ADF serves as a good estimate of digestibility, IVID provides a more accurate assessment of a forage's feeding value by actually measuring the portion of a forage that is digested. This process is more expensive and time consuming than the analysis for ADF concentrations of a feed, but provides a more meaningful measure of forage digestibility. Techniques for measuring in vitro digestibility are based on incubating a forage sample in a solution containing rumen microorganisms for an extended period of time (usually 48 hours).

Linkage: A phenomenon wherein alleles on the same chromosome tend to segregate together more often than expected by chance if their transmission was independent.

Marker: A readily detectable phenotype, preferably inherited in co-dominant fashion (both alleles at a locus in a diploid heterozygote are readily detectable), with no environmental variance component, i.e., heritability of 1.

Milk Per Acre: A measurement that combines "milk per ton" and "dry matter yield per acre" that is widely used as an estimate of the economic value of a forage.

Milk Per Ton: A measurement that characterizes forage quality in which the ratio of milk produced to forage consumed is estimated. The initial equation that was used to calculate "milk per ton" relied primarily on ADF and NDF as estimates of the energy content and potential intake of the forage, respectively. After subtracting the amount of energy required for daily maintenance of the cow, the quantity of milk that could be produced from the remaining energy is calculated. The ratio of milk produced to forage consumed is then reported in the units of pounds of milk produced per ton of forage consumed. The standard equation for "milk per ton" has since been modified multiple times to increase accuracy and each of these modified equations are well known in the art. For instance, the MILK2006 formula uses forage analyses, e.g., crude protein, NDF, in vitro NDF digestibility, and non-fiber carbohydrate (NFC), to estimate both forage energy content and DM intake from NDF.

NAAIC: The abbreviation for the North America Alfalfa Improvement Conference, which is the governing body of the NA&MLVRB.

NA&MLVRB: The abbreviation for the National Alfalfa and Miscellaneous Legume Variety Review Board. The NA&MLVRB is administered by the Association of Official Seed Certifying Agencies (AOSCA) and was previously known as the National Alfalfa Variety Review Board (NAVRB).

Neutral-Detergent Fiber (NDF): A measurement that represents the total amount of fiber present in the alfalfa. Because fiber is the portion of the plant most slowly digested in the rumen, it is this fraction that fills the rumen and becomes a limit to the amount of feed an animal can consume. The higher the NDF concentration of a forage, the slower the rumen will empty reducing what an animal will be able to consume. For this reason, NDF is used by nutritionists as an estimate of the quantity of forage that an animal will be able to consume. Forages with high NDF levels can limit intake to the point that an animal is unable to consume enough feed to meet their energy and protein requirements.

Or: As used herein is meant to mean "and/or" and be interchangeable therewith unless explicitly indicated to refer to the alternative only.

Persistence: The quality of the alfalfa stand in terms of both plant health and the number of plants over seasons. Persistence of an alfalfa variety is measured, typically in its area of adaptation, by visually estimating percent ground cover both in the establishment year ("Initial") and at least 24 months later ("Final").

Phenotype: The detectable characteristics of a cell or organism, which are the manifestation of gene expression.

Phenotypic Score (PSC): The phenotypic score is a visual rating of the general appearance of the variety. All visual traits are considered in the score, including healthiness, standability, appearance, and freedom from disease. Ratings are scored as 1 being poor to 9 being excellent.

Potato Leafhopper Resistance: A reaction of the alfalfa host plant which enables it to avoid serious damage from potato leafhopper feeding. A resistant plant demonstrates normal growth despite the feeding of potato leafhoppers. Susceptible plants show significant stunting and yellowing as a result of potato leafhopper feeding. Potato leafhopper resistance of alfalfa cultivars is characterized as a combination of percent resistance and average severity index (ASI). The National Alfalfa Variety Review Board has adopted a rating system based on percent of resistant plants to describe levels of pest. The ratings are susceptible (0-5%); low resistance (6-15%); moderate resistance (16-30%); resistance (31-50%); and high resistance (>51%). The average severity index (ASI) of a variety is the average damage score for 100 random plants. Individual plants are scored on a (1-5) scale, where "1" corresponds to "no damage evident" and "5" corresponds to "severe stunting and yellowing." Plants scored as "1" and "2" are classified as resistant.

Quantitative Trait Loci (QTL): Genetic loci that contribute, at least in part, certain numerically representable traits that are usually continuously distributed.

Regeneration: The development of a plant from tissue culture.

Relative Feed Value (RFV) is a numeric value assigned to forages based upon their ADF and NDF values. In this calculation, NDF is used to estimate the dry matter intake expected for a given forage, and the ADF concentration is used to estimate the digestibility of the forage. By combining these two relationships, an estimate of digestible dry matter intake is generated. This value is then reported relative to a standard forage (fall bloom alfalfa=100), and can be used to rank forages based on their anticipated feeding value. Relative feed value has been accepted in many areas as a means of estimating forage feeding value and is commonly used in determining the price of alfalfa at tested hay auctions.

Relative Forage Quality (RFQ): A numeric value that estimates the energy content of forage for total digestible nutrients as recommended by the National Research Council. Values are assigned to forages based upon the dry matter intake (DMI), which can be estimated by NDF, and Total Digestible Nutrients (TDN). By combining these two relationships, an estimate of how the forage will perform in animal rations is predicted. Relative forage quality has been accepted in many areas as a means of estimating forage feeding value and is commonly used in determining the price of alfalfa at tested hay auctions or for on farm use.

Self-pollination: The transfer of pollen from the anther to the stigma of the same plant.

Single Locus Converted (Conversion) Plant: Plants that are developed by a plant breeding technique called backcrossing and/or by genetic transformation to introduce a given locus that may be transgenic in origin, in which essentially all of the morphological and physiological characteristics of an alfalfa variety are recovered in addition to the characteristics of the locus transferred into the alfalfa variety via the backcrossing technique or by genetic transformation. It is understood that once introduced into any alfalfa plant genome, a locus that is transgenic in origin (transgene), can be introduced by backcrossing as with any other locus. A single locus may comprise one gene, or in the case of transgenic plants, one or more transgenes integrated into the host genome at a single site (locus).

SNP profile: A profile in which single nucleotide polymorphisms (SNPs) are used as genetic markers. SNP detection methods that may be used to generate such a profile are well-known in the art and include, but are not limited to, dynamic allele-specific hybridization, molecular beacons, microarrays, restriction enzyme digestions, tetra-primer amplification refractory mutation system PCR, primer extension, TaqMan, and next-generation sequencing.

SSR profile: A profile of simple sequence repeats used as genetic markers and scored by gel electrophoresis following PCR amplification using flanking oligonucleotide primers.

Substantially Equivalent: A characteristic that, when compared, does not show a statistically significant difference from the mean, e.g., p=0.05.

Synthetic variety 1 (SYN1): A variety that is developed by intercrossing a number of genotypes with specific favorable characteristics and/or overall general favorable qualities. Synthetic (SYN) varieties can be developed by using clones, inbreds, open-pollinated varieties, and/or individual heterozygous plants.

Synthetic variety 1+n (SYN(1+n)): A variety that descends from a Syn1 and is produced by randomly intercrossing plants of the previous generation so that allele frequencies are maintained from one generation to the next. For example, a Syn2 is produced by randomly crossing Syn1 plants, and randomly crossing those Syn2 plants produces a Syn3.

Tons per Acre (TA): A measurement of the tons of alfalfa produced per acre of land, which is used to calculate yield. Typically this measurement is made using harvested alfalfa that has been dried, which may be denoted as "DM in T/A" or "Tons DM/Acre."

Tissue Culture: A composition comprising isolated cells of the same or a different type or a collection of such cells organized into parts of a plant.

Total Digestible Nutrients (TDN): An estimate of the energy content of a feedstuff based on its relative proportions of fiber, fat, carbohydrate, crude protein, and ash. Because it is expensive to measure each of these components, TDN is usually estimated from ADF or IVTD. Although still used in some areas as a criteria for evaluating alfalfa hay at auctions, TDN has been shown to overestimate the energy content of low quality forages and thus does not accurately reflect the nutritional value of all forage samples.

Transgene: A genetic sequence that has been introduced into the genome of a alfalfa plant by transformation or site-specific recombination.

Winterhardiness (WH): An estimate of the ability of an alfalfa plant to survive the stresses associated with winter. Cold hardiness is a key feature of the winterhardiness trait. There is a general relationship between fall dormancy and winterhardiness, the early fall dormant types (FD2-5) are more winterhardy than the later fall dormant types (FD6-9). The winterhardiness rating used in this patent are derived from the standard test for measuring winter survival. The standard test measures plant survival and spring vigor following a winter stress enough to substantially injure check varieties.

TABLE 16

Check Cultivar Fall Dormancy Ratings (FDR) and
Fall Dormancy Classes (FDC).

| VARIETY | FDR[1] | FDC[2] |
|---|---|---|
| Maverick | 0.8 | 1.0 |
| Vernal | 2.0 | 2.0 |
| 5246 | 3.4 | 3.0 |
| Legend | 3.8 | 4.0 |
| Archer | 5.3 | 5.0 |
| ABI 700 | 6.3 | 6.0 |
| Doria Ana | 6.7 | 7.0 |
| Pierce | 7.8 | 8.0 |
| CUF 101 | 8.9 | 9.0 |
| UC 1887 | 9.9 | 10.0 |
| UC 1465 | 11.2 | 11.0 |

[1]The FDR number corresponds to the value calculated using the University of California regression equation.
[2]The FDC number corresponds to fall dormancy class used by the Certified Alfalfa Seed Council (CASC).

DEPOSIT INFORMATION

A deposit of alfalfa variety 412A122, which is disclosed herein above and referenced in the claims, was made with the Provasoli-Guillard National Center for Marine Algae and Microbiota, Bigelow Laboratory for Ocean Science (NCMA), 60 Bigelow Drive, East Boothbay, Me. 04544. The date of deposit is Feb. 12, 2020 and the accession number for those deposited seeds of alfalfa variety 412A122 is NCMA Accession No. 202002003. All restrictions upon the deposit have been removed, and the deposit is intended to meet all of the requirements of the Budapest Treaty and 37 C.F.R. § 1.801-1.809. The deposit will be maintained in the depository for a period of 30 years, or 5 years after the last request, or for the effective life of the patent, whichever is longer, and will be replaced if necessary during that period.

All of the compositions and methods disclosed and claimed herein can be made and executed without undue experimentation in light of the present disclosure. While the compositions and methods of this invention have been described in terms of the foregoing illustrative embodiments, it will be apparent to those of skill in the art that variations, changes, modifications, and alterations may be applied to the composition, methods, and in the steps or in the sequence of steps of the methods described herein, without departing from the true concept, spirit, and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

The references cited herein, to the extent that they provide exemplary procedural or other details supplementary to those set forth herein, are specifically incorporated herein by reference.

What is claimed:

1. A seed of alfalfa variety 412A122, wherein representative seed of said alfalfa variety have been deposited under NCMA Accession No. 202002003.

2. A plant grown from the seed of claim 1 or a plant part thereof, wherein the plant part comprises at least one cell of said alfalfa variety 412A122.

3. A tissue culture of regenerable cells or regenerable protoplasts from the plant or plant part of claim 2.

4. The tissue culture according to claim 3, comprising cells or protoplasts from a plant part selected from the group consisting of leaves, roots, root tips, root hairs, anthers, pistils, stamens, pollen, ovules, flowers, seeds, embryos, stems, buds, cotyledons, hypocotyls, cells, and protoplasts.

5. An alfalfa plant regenerated from the tissue culture of claim 3, wherein the regenerated plant has all of the physiological and morphological characteristics of a plant of said alfalfa variety 412A122.

6. A composition comprising the seed of claim 1 that is comprised in plant seed growth media.

7. The composition of claim 6, wherein the plant seed growth media is soil or a synthetic cultivation media.

8. A method for producing a first generation progeny alfalfa seed, the method comprising crossing the plant of claim 2 with itself or a second alfalfa plant and harvesting the resultant alfalfa seed.

9. The method of claim 8, wherein the second alfalfa plant is a plant of alfalfa variety 412A122; wherein representative seed of said alfalfa variety have been deposited under NCMA Accession No. 202002003.

10. A first generation progeny alfalfa seed produced by the method of claim 8; wherein the first generation progeny alfalfa seed has all of the physiological and morphological characteristics of a seed of said alfalfa variety 412A122.

11. An alfalfa plant produced by growing the seed of claim 10; wherein the plant produced has all of the physiological and morphological characteristics of a plant of said alfalfa variety 412A122.

12. A method of vegetatively propagating the plant of claim 2, the method comprising the steps of:
    (a) collecting a tissue capable of being propagated from the plant;
    (b) cultivating the tissue to obtain proliferated shoots; and
    (c) rooting the proliferated shoots to obtain rooted plantlets.

13. The method of claim 12, further comprising growing a plant from the rooted plantlets.

14. A method of modifying an alfalfa plant, wherein the method comprises introducing a transgene or a single locus conversion into the plant of claim 2.

15. The alfalfa plant produced by the method of claim 14; wherein the alfalfa plant produced otherwise comprises all of the physiological and morphological characteristics of a plant of said alfalfa variety 412A122.

16. The plant of claim 15, wherein the transgene or single locus comprises a nucleic acid sequence that enables site-specific genetic recombination or confers a trait selected from the group consisting of male sterility, herbicide tolerance, insect resistance, pest resistance, disease resistance, improved digestibility, improved energy content, improved forage or seed yield, improved winterhardiness, improved nitrogen fixation, modified fatty acid metabolism, abiotic stress resistance, flowering time, altered seed amino acid composition, and modified carbohydrate metabolism.

17. A seed that produces the plant of claim 15; wherein the seed otherwise comprises all of the physiological and morphological characteristics of a seed of said alfalfa variety 412A122.

18. A method of introducing a single-locus conversion into the plant of claim 2, the method comprising:
    (a) crossing said plant with a second alfalfa plant to produce a first generation of progeny plants, wherein the second alfalfa plant comprises the single locus; and (b) selecting a progeny plant that comprises the single locus.

19. The method of claim 18, wherein the single locus comprises a transgene.

20. An alfalfa plant produced by the method of claim 18; wherein the alfalfa plant produced otherwise comprises all of the physiological and morphological characteristics of a plant of said alfalfa variety 412A122.

21. A seed that produces the plant of claim 20; wherein the seed otherwise comprises all of the physiological and morphological characteristics of a seed of said alfalfa variety 412A122.

22. A method for introducing a transgene or a single locus conversion into a population of alfalfa plants, the method comprising the steps of:
  (a) modifying the plant of claim 2 by introducing a transgene or a single locus conversion; and
  (b) crossing the modified alfalfa plant of step (a) with a population of alfalfa plants to produce a population of progeny plants, wherein at least a progeny plant comprises the transgene or single locus conversion.

23. The method of claim 22, further comprising the step of:
  (c) applying a selection technique to the population produced in step (b) to select said progeny plants that comprise the transgene or single locus conversion.

24. A method of producing a synthetic alfalfa variety, the method comprising combining the seed of claim 1 with seed of a second alfalfa variety.

25. A method of producing a commodity plant product, the method comprising producing the commodity plant product from the plant of claim 2.

26. The method of claim 25, wherein the commodity plant product is selected from a group consisting of sprouts, forage, hay, greenchop, and silage.

27. A commodity plant product produced by the method of claim 25, wherein the commodity plant product comprises at least one cell of said alfalfa variety 412A122.

* * * * *